(12) United States Patent
Walter et al.

(10) Patent No.: US 8,353,232 B2
(45) Date of Patent: Jan. 15, 2013

(54) DEVICE AND METHOD FOR BRAKING A SHAFT OF A MICROTOME

(75) Inventors: Roland Walter, Neulussheim (DE); Stefan Thiem, Heidelberg (DE); Andreas Laudat, Meckesheim (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 442 days.

(21) Appl. No.: 12/602,183

(22) PCT Filed: Jun. 6, 2008

(86) PCT No.: PCT/EP2008/057074
§ 371 (c)(1),
(2), (4) Date: Nov. 30, 2009

(87) PCT Pub. No.: WO2008/148871
PCT Pub. Date: Dec. 11, 2008

(65) Prior Publication Data
US 2010/0180742 A1 Jul. 22, 2010

(51) Int. Cl.
*B26D 1/00* (2006.01)
*B23Q 15/00* (2006.01)
(52) U.S. Cl. .............................. 83/13; 83/915.5; 83/72
(58) Field of Classification Search .................... 83/76.9, 83/68, 915.5
See application file for complete search history.

(56) References Cited

U.S. PATENT DOCUMENTS

| | | | | |
|---|---|---|---|---|
| 3,212,379 A | * | 10/1965 | McCormick et al. | 83/167 |
| 3,699,830 A | * | 10/1972 | Pickett | 83/13 |
| 3,926,085 A | * | 12/1975 | Shatzel | 83/718 |
| 4,181,206 A | * | 1/1980 | Seilenbinder | 477/174 |

(Continued)

FOREIGN PATENT DOCUMENTS
DE 92 19 220 U1 9/2000

OTHER PUBLICATIONS

The International Bureau of WIPO, International Preliminary Report on Patentability (English Translation), International Application No. PCT/EP2008/057074, Jan. 12, 2010, Switzerland.

*Primary Examiner* — Sean Michalski
(74) *Attorney, Agent, or Firm* — Hodgson Russ LLP

(57) ABSTRACT

The present invention relates to a device for braking or locking a shaft (6) of a microtome (1). The microtome (1) comprises the shaft (6), an actuating element (2), a movement mechanism (37) and a housing (38). With the movement mechanism (37) an object to be cut can be moved relative to a knife blade. The actuating element (2) can be manually actuated by an operator. As a result thereof, the shaft (6) can be rotated. Via the shaft (6), the movement mechanism (37) for performing the relative motion between the object and the knife blade can be driven. Further, the present invention relates to a method for operating a device for braking a shaft (6) of a microtome (1). So that the device can be used in a mechanically formed movement mechanism (37), the inventive device is characterized by an actuator and a braking unit (25). The braking unit (25) is connected in a rotatably fixed manner to the shaft (6). With the actuator, the braking unit (25) can be automatically placed in a brake position in which the shaft (6) can be connected in a rotatably fixed manner to the housing (11).

20 Claims, 6 Drawing Sheets

U.S. PATENT DOCUMENTS

Figure 1:
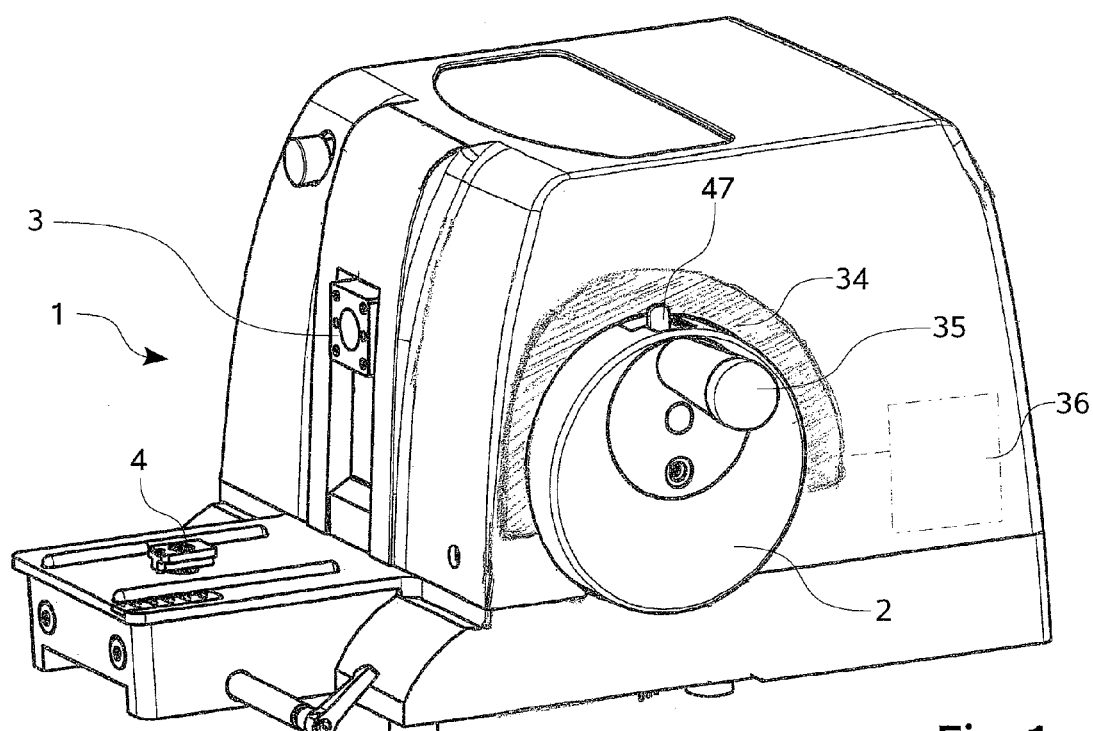

| | | | |
|---|---|---|---|
| 4,839,533 A * | 6/1989 | Aga | 307/140 |
| 5,043,907 A * | 8/1991 | Richards | 700/167 |
| 5,065,657 A * | 11/1991 | Pfeifer | 83/703 |
| 5,181,443 A * | 1/1993 | Sitte et al. | 83/72 |
| 5,197,361 A * | 3/1993 | Carrier et al. | 82/1.2 |
| 5,226,335 A * | 7/1993 | Sitte et al. | 83/74 |
| 5,461,953 A * | 10/1995 | McCormick | 83/36 |
| 5,630,487 A * | 5/1997 | Hamman et al. | 188/353 |
| 5,761,977 A * | 6/1998 | Jakobi et al. | 83/13 |
| 5,960,690 A * | 10/1999 | Romi | 82/133 |
| 6,598,507 B1 * | 7/2003 | Gunther et al. | 83/76.9 |
| 7,111,535 B2 * | 9/2006 | Hess | 83/57 |
| 7,146,895 B2 * | 12/2006 | Kong et al. | 83/705 |
| 7,900,545 B2 * | 3/2011 | Schneider | 83/331 |
| 2006/0272467 A1 * | 12/2006 | Hendrick et al. | 83/730 |
| 2007/0180965 A1 * | 8/2007 | Ito et al. | 83/73 |
| 2008/0091309 A1 * | 4/2008 | Walker | 701/1 |

* cited by examiner

DEVICE AND METHOD FOR BRAKING A SHAFT OF A MICROTOME

The present invention relates to a device for braking or locking a shaft of a microtome. The microtome comprises the shaft, an actuating element, a movement mechanism and a housing. By means of the movement mechanism an object to be cut can be moved relative to a knife blade. The actuating element can be manually actuated by an operator. As a result thereof, the shaft can be rotated. Via the shaft, the movement mechanism for performing the relative motion between the object and the knife blade can be driven. The actuating element can be designed in the form of a handwheel. Further, the present invention relates to a method for operating a device for braking a shaft of a microtome.

Microtomes have been known from the prior art for a long time. By means of a microtome, fine tissue sections can be produced from a tissue sample embedded in paraffin, which sections can then be placed on a slide for microscopic examination. There are microtomes in which the object—except for a feed motion—is clamped in a holder on the housing of the microtome so as to be immovable, and in which the knife blade is moved relative to the object or, respectively, to the microtome housing. This is particularly the case for slide microtomes and disc microtomes.

In the case of rotary microtomes—except for a feed motion—the knife blade is arranged fixed to the housing and the clamped object is arranged movably relative to the knife blade. The movement mechanism of a rotary microtome can be driven mechanically or can be motor-driven, for example, by means of an electric motor. When working with the microtome, it is, inter alia, necessary to adjust the object or the tissue sample at the clamping device for the embedded tissue sample—the so-called object head—or to clamp another tissue sample. If the object head is arranged freely movably, it may happen that the operator cuts himself/herself. This is particularly disadvantageous as the tissue samples usually contain contaminated or bacterially contaminated biological material, and thus there is an acute risk of infection for the operator of the microtome. This is why the movable parts of the object head can be arrested or locked.

Thus, for example, from DE 199 11 163 C1 a movement mechanism for moving the object head is known, which mechanism is driven by an electric motor. Here, an automatic blocking or locking of the object head is caused by a direct blocking of the drive or, respectively, the electric motor. In case a microtome does not have an electric drive, a locking lever mechanically actuated by an operator could be provided on or near the actuating element or handwheel, by means of which the handwheel and thus the movement mechanism and eventually also the object head can be locked. Such a locking lever is shown in FIG. 1 indicated by the reference sign 47 and is—per se—known from the prior art. This, however, requires an additional hand movement or work step of the operator so that this locking possibility is not used by all operators.

Therefore, the object of the present invention is to specify and develop a device for braking a microtome, which device can be used in a mechanically designed movement mechanism.

The inventive device of the type mentioned at the beginning solves the above object by the features of claim 1. Accordingly, such a device is characterized by an actuator and a braking unit. The braking unit is connected in a rotatably fixed manner to the shaft. By means of the actuator, the braking unit can automatically be placed into a brake position in which the shaft can be connected in a rotatably fixed manner to the housing or a component part fixed to the housing. In this connection, automatic placement in particular means that the braking unit can be placed into the brake position according to a control logic if a predeterminable condition is met or not met.

It has first of all been found that a device for braking the relative motion between the object and the knife blade can in particular be made available by the inventive provision of an actuator and a braking unit when the movement mechanism is driven by the actuating element purely mechanically. In this case, it is not possible by any means to brake the relative motion in that a holding torque is applied to a non-provided motor drive. But even given a motor drive of the movement mechanism, the inventive device can be used, should this, for example, be necessary for reasons of redundancy for avoiding the risk of injury of the operator and/or for safety reasons.

In particular, given a rotary microtome the rotary position of the actuating element has a fixed relation to the position of the object. Thus, also the interacting component parts for transferring the motion of the actuating element onto the movement mechanism have a defined and unchangeable relation. Insofar it could thus be provided to provide the brake at any of these component parts. Since according to the invention, the braking unit is provided on the shaft which drives the movement mechanism for performing the relative motion, the shaft and thus the movement mechanism can advantageously be braked in every situation or position, i.e. not only in the highest position of the object where, for example, the vertical movement of the object head could be blocked. Further, the device for braking can advantageously be realized with simple and cost-efficient means since only the actuator and the braking unit have to be provided at a suitable position of the microtome.

The braking unit could be frictionally engaged or positively engaged with the housing or a component part fixed to the housing in the brake position. Since in the case of a microtome the operator usually does not actuate the actuating element with excessive force, it can be assumed that the shaft does not have to transmit a high torque. Therefore, it can be sufficient to provide a frictional engagement between the braking unit and the housing or, respectively, the component part fixed to the housing. Nevertheless, preferably a positive engagement between the braking unit and the housing is provided in order to effectively block the shaft and thus the actuating element as well. Compared to the frictional engagement, by means of the positive engagement between the braking unit and the housing or a component part fixed to the housing usually a higher force has to be exerted on the actuating element in order to cause a "slipping" or a release of the brake.

According to a preferred embodiment the braking unit has a component part, in particular a sleeve or a spur wheel. The component part could have a toothing in radial or axial direction. Preferably, it is provided that the component part has a toothing extending in axial direction. The toothing engages with a toothing that is substantially complementarily formed and provided on the housing or the component part fixed to the housing if the braking unit is in the brake position. Since the braking unit is connected in a rotatably fixed manner to the shaft, the component part is in this embodiment connected to the shaft in a rotatably fixed and positive manner.

It is basically feasible that a hydraulic cylinder or a pneumatic cylinder could be provided as an actuator. Preferably, however, the actuator has an electromagnet with which the braking unit can be moved. An electromagnet can be installed in a microtome in a relatively easy and cost-efficient manner since the required energy supply, electric current, is usually available. The actuator designed in the form of an electromagnet could be arranged such that the braking unit is attracted by the actuator.

The braking unit could now be biased such that the braking unit is forced into the brake position and that the actuator counteracts the biasing force when the braking unit is moved out of the brake position. Alternatively, the braking unit could be biased such that the braking unit is forced out of the brake position and that the actuator counteracts the biasing force when placing the braking unit into the brake position. The biasing could be generated by means of a spring which is suitably arranged between the braking unit and a component part of the microtome fixed to the housing.

Basically, the control of the actuator for automatically placing the braking unit into the brake position could be controlled depending on different operating parameters of the microtome. According to a particularly preferred embodiment it is provided to control the actuator depending on the actuation of the actuating element by the operator. For this, an actuating unit is provided with which it can be determined or detected whether the operator manually actuates the actuating element. In this case, the actuator can be controlled such that the braking unit can be moved out of the brake position. The brake is then not activated or, respectively, the relative motion between the object and the knife blade cannot be locked since the operator of the microtome actuates the actuating element. Then he/she controls the movement mechanism for relative motion between the object and the knife blade via the actuating element. Insofar it is quite unlikely that he/she simultaneously works on the object to be cut or on the object head. Therefore, in this case there is no acute risk of injury for the operator, which would require a locking of the object. Consequently, according to the preferred embodiment the actuation or the contact of the actuating element is detected or determined by means of an actuating unit and, depending on whether an actuation of the actuating element can be determined with the actuating unit or whether an actuation cannot be determined, the brake is controlled. By this way of proceeding it is advantageously not necessary to provide a locking lever which, with an additional action of the operator, has to be actuated each time during locking and unlocking of the brake. In all, the operation of the microtome is thus facilitated and the ease and convenience in operation are increased. The safety during the operation of the microtome can also be considerably increased as a result thereof, since the operator does not have to perform an additional hand movement in order to lock or release the brake and, accordingly, a possible inadvertence of the operator does no longer pose a safety risk or a risk of injury.

The actuating unit could be based on a mechanical or an electrical detection principle. If the actuating unit is based on a mechanical detection principle, according to a preferred embodiment the actuating unit could have a first coupling area which can be engaged with a second coupling area. The second coupling area is connected to the actuating element in a rotatably fixed manner. The two coupling areas are engaged with one another when the braking unit is not engaged with the housing. In this operating state, the brake is deactivated and the actuating element drives the shaft with which in turn the movement mechanism can be driven. In this operating state, it is thus not to be detected whether a non-actuated actuating element is to be actuated again.

The actuating unit could be connected in a rotatably fixed manner to the shaft, for example, when the actuating element is mounted directly on the shaft. The actuating unit could then be mounted rotatably with respect to the actuating element if the two coupling areas are not engaged with one another. In this operating state, the actuating unit can detect whether the operator actuates the actuating element. This can be useful when the brake is activated.

Preferably it is provided that the rotation between the actuating element and the actuating unit can be limited for example, by means of stops. The stops could be mounted such that a rotation between the actuating element and the actuating unit of a maximum of +/−5 degrees is possible. By means of the actuating unit, it is above all to be detected whether the actuating element is actuated. For this, a relative rotation by a small angle is sufficient.

At least one biasing means could be provided with which a rotation between the actuating unit and the actuating element can be forced into a predeterminable position. Preferably, the at least one means forces the actuating unit into a centered relative position with respect to the actuating element. Thus, an actuation of the actuating element in two opposite directions can be detected.

The at least one biasing means can have a spring which on the one end acts on the actuating unit and which on the other end acts on the actuating element. Preferably, two springs are provided and arranged such that the one spring causes a rotation between the actuating unit and the actuating element in a direction of rotation which is substantially opposite to the direction of rotation that is effected by the other spring. As a result thereof, a biasing means can be realized which causes a centered biasing with respect to the rotation between the actuating unit and the actuating element.

Specifically, the actuating unit could be connected in a rotatably fixed manner to the braking unit if the actuating unit and the braking unit are two different component parts. Alternatively, the actuating unit could be integrally formed with the braking unit. This advantageously favors a compact construction.

Further, a movement sensor could be provided with which a movement of the actuating element or the actuating unit can be detected. The movement sensor could have an incremental encoder or an angle encoder provided on the actuating element. It is likewise feasible that on the actuating element a toothing is provided which meshes with a toothed gear on which an incremental encoder or an angle encoder is provided.

Preferably, a control unit could be provided, which is—preferably electronically-connected to the actuator and the movement sensor. The control unit could have a printed circuit board with electronic components and an electrical circuit. The control unit could be arranged within the microtome housing and/or near the actuating unit.

If the actuating unit is based on an electrical detection principle, the actuating unit could have at least one sensor unit which is provided on the actuating element and/or adjacent to the actuating element or on the housing of the microtome. With the sensor unit, a contact by the operator can be determined. The brake can be automatically controlled depending on a contact by the operator determined or not determined by the at least one sensor unit.

The sensor unit could have an electrically conductive area. The electrically conductive area is arranged electronically insulated relative to further components of the microtome. The electrically conductive area is connected to an electrical circuit. By means of the electrical circuit, a contact of the electrically conductive area can be determined. The electrically conductive area could have a hot embossing foil of stainless steel, which foil could be arranged on the outer surface of the microtome housing in an area which is adjacent to the actuating element. Advantageously, the hot embossing foil of stainless steel can be directly adapted to the shape of the housing since it can be formed flexibly.

In principle, the sensor unit can have a proximity sensor or a contact sensor or, respectively, touch sensor. In one embodiment, it could be provided that with the aid of the proximity sensor it can be detected that a contact by the operator is to be expected if the approach of the hand of the operator below a predeterminable distance value is determined. Additionally or alternatively, it could be provided that an operator actually has to contact the actuating element so that the brake is controlled in accordance with the control logic. A foil contact sensor could in particular be provided as the touch sensor. A proximity sensor will usually have a capacitive sensor.

Specifically, the actuating element could have a handwheel. The actuating element is connected in a rotatably fixed manner to a shaft or axle indirectly or directly driving the movement mechanism. The shaft is rotatably mounted relative to the microtome housing by means of at least one bearing. Such a design is in particular functional in the case of a rotary microtome. Now, a sensor unit could be arranged on the surface of the actuating element or, respectively, the handwheel. Thus, the sensor unit or, respectively, the part of the sensor unit with which an approach or a contact by the operator can be detected moves together with the actuating element. In other words, the actuating element could have a hot embossing foil of stainless steel. A corresponding electronic circuit could either be arranged inside the actuating element—likewise moving together with the actuating element. Alternatively, such a circuit could be arranged stationarily inside the microtome. So that the sensor unit as well as the actuating element have the same electrical potential, the shaft could be designed electrically conductive and have an electrically non-conductive area. The electrically non-conductive area could now be arranged such that an electric conductivity is given between the sensor unit, the conductive area of the shaft and the bearing. Further, it would be necessary that an electric insulation is provided between further components of the microtome and the sensor unit, the conductive area of the shaft and the bearing. The electrically non-conductive area could have a non-conductive plastic area in the longitudinal direction of the shaft, i.e. in axial direction. Alternatively, it could also be provided that the shaft has, for example, a hollow cylindrical-shaped plastic area in radial direction, over which area a conductively designed hollow shaft area extends in parts.

In principle, the microtome could be provided in the form of a rotary microtome, a slide microtome, a vibratome or a disc microtome. In particular, it could be provided that the microtome is designed in the form of a cryostat microtome, where the object, the knife blade and the movement mechanism are arranged in a cooled cryo chamber, and the actuating element can be manually actuated from the outside. A sensor unit would have to be provided on the actuating element which can be accessed from the outside.

With regard to a method, the object mentioned at the beginning is solved by the features of claim 22. Accordingly, a method for controlling a device for braking a shaft of a microtome is defined. The microtome comprises the shaft, an actuating element, a movement mechanism and a housing. With the movement mechanism, an object to be cut is moved relative to a knife blade. The actuating element is manually actuated by an operator. As a result thereof, the shaft is rotated. Via the shaft the movement mechanism for performing the relative motion between the object and the knife blade is driven. The inventive method is characterized by an actuator and a braking unit. The braking unit is connected to the shaft in a rotatably fixed manner. With the actuator the braking unit is automatically placed in a brake position, in which the shaft is connected in a rotatably fixed manner to the housing or a component part fixed to the housing.

The method according to the invention is particularly suitable for operating a device according to one of the claims 1 to 21 so that, for avoiding repetitions with regard to the device features on this matter, reference is made to the preceding part of the description. In this connection, the method steps required for operating the device become evident to the person skilled in the present art in knowledge of the disclosure of the preceding part of the description.

There are different possibilities of configuring and developing the teaching of the present invention in an advantageous manner. Reference is to be made, on the one hand, to the claims which are dependent on claim 1 and, on the other hand, to the following explanation of the preferred embodiments of the invention with reference to the drawing. In connection with the explanation of the preferred embodiments of the invention with reference to the drawing, also generally preferred embodiments and developments of the teaching are explained.

FIG. 1 schematically shows in a perspective view a first embodiment of a microtome with an inventive device for braking a shaft.

Figure 2:
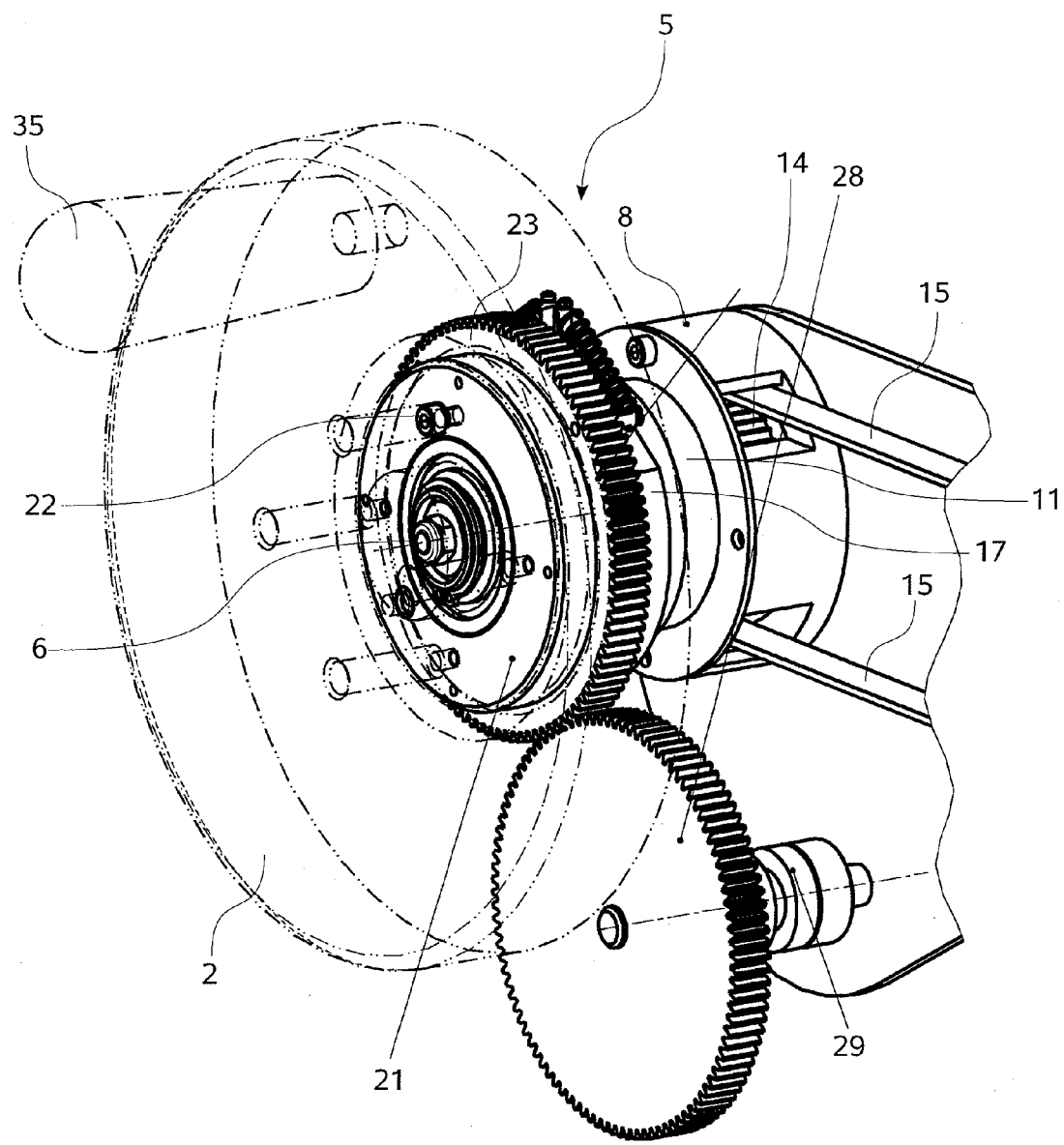

FIG. 2 schematically shows in a perspective view a part of a microtome with an inventive device for braking a shaft.

Figure 3:
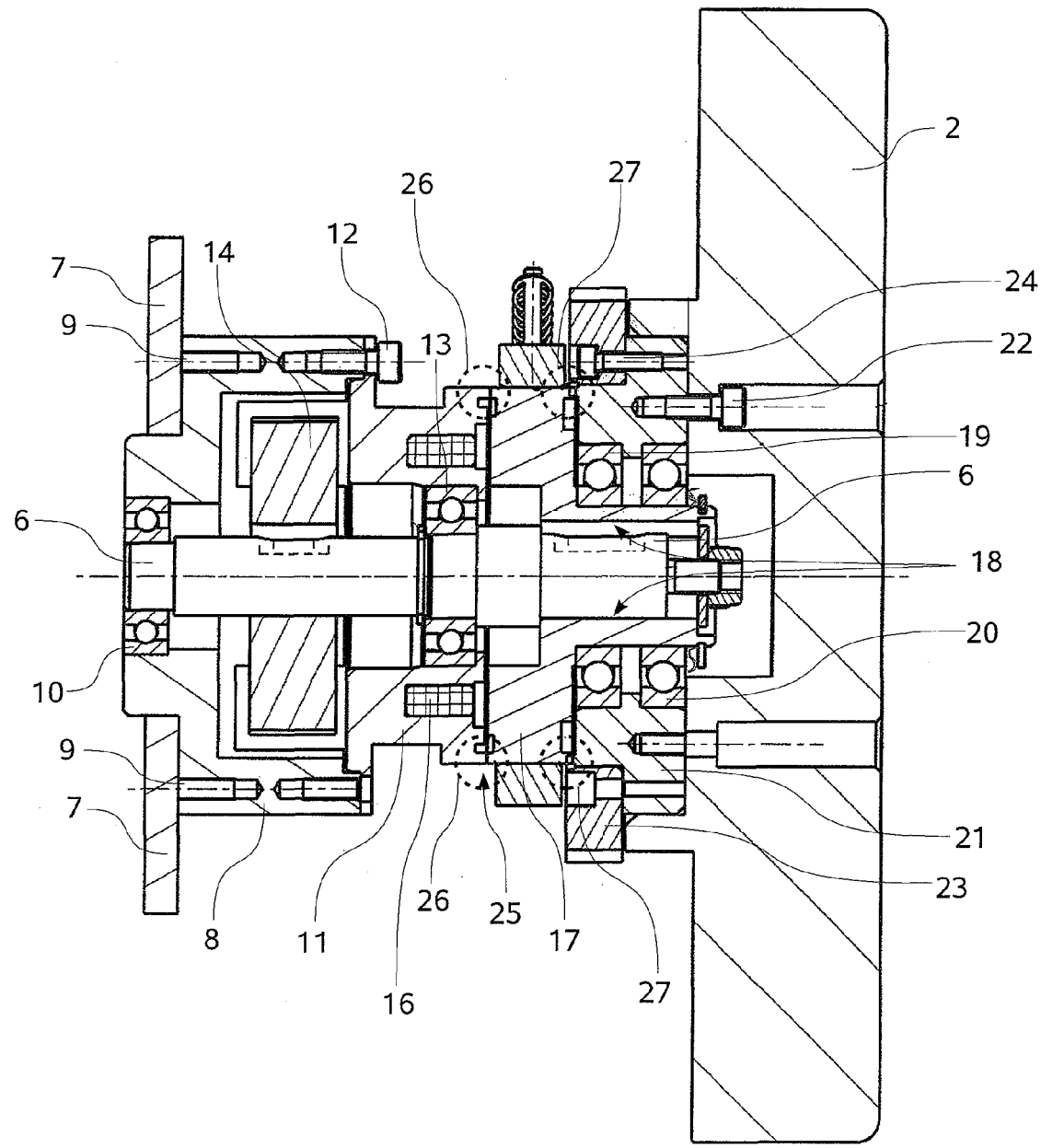

FIG. 3 schematically shows in a sectional view the components of FIG. 2.

Figure 4:
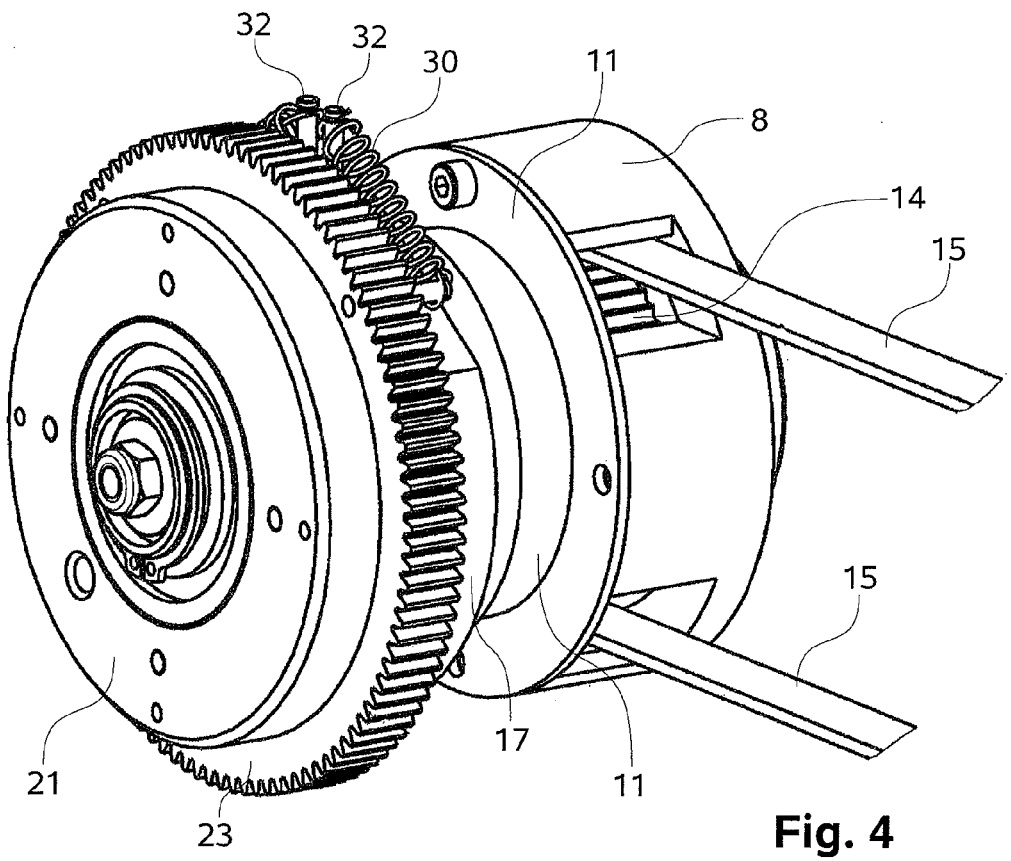

FIG. 4 schematically shows in a perspective view a part of the assembly of FIG. 2.

Figure 5:
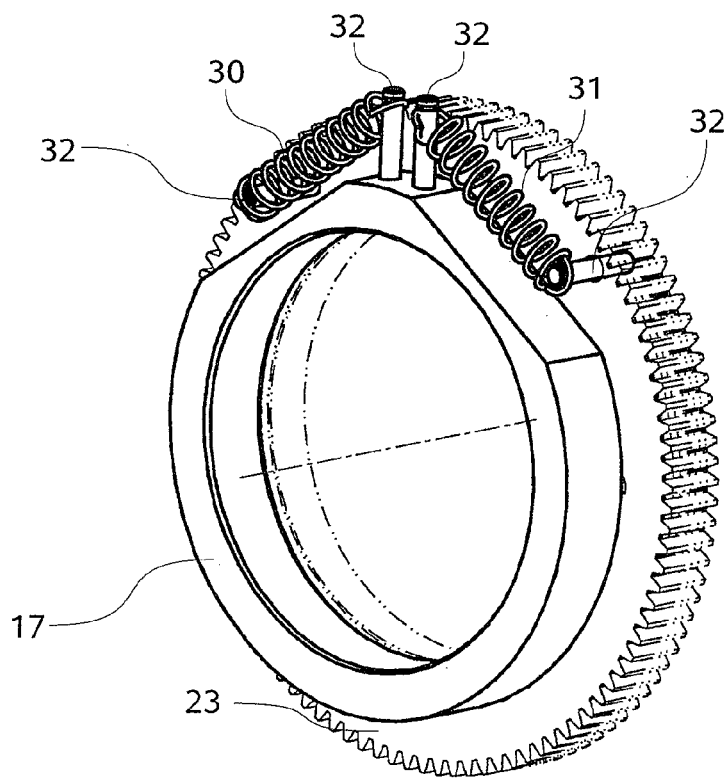

FIG. 5 schematically shows in a perspective view an embodiment of a part of the actuating unit.

Figure 6:
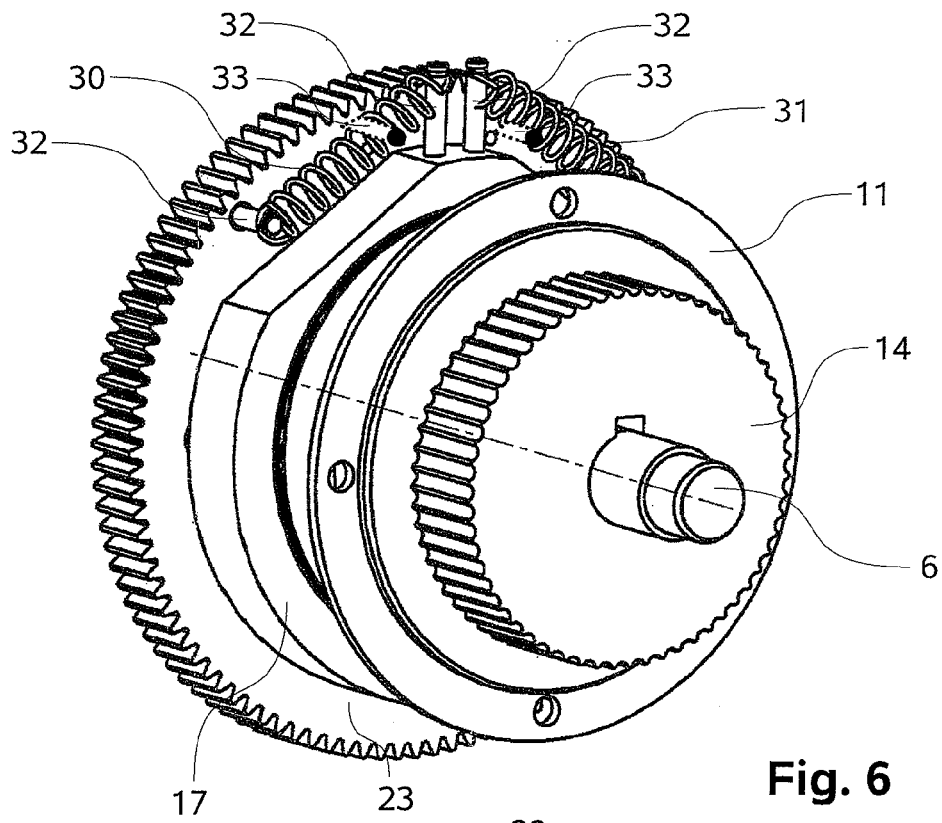

FIG. 6 schematically shows in a perspective view a part of the assembly of FIG. 4.

Figure 7:
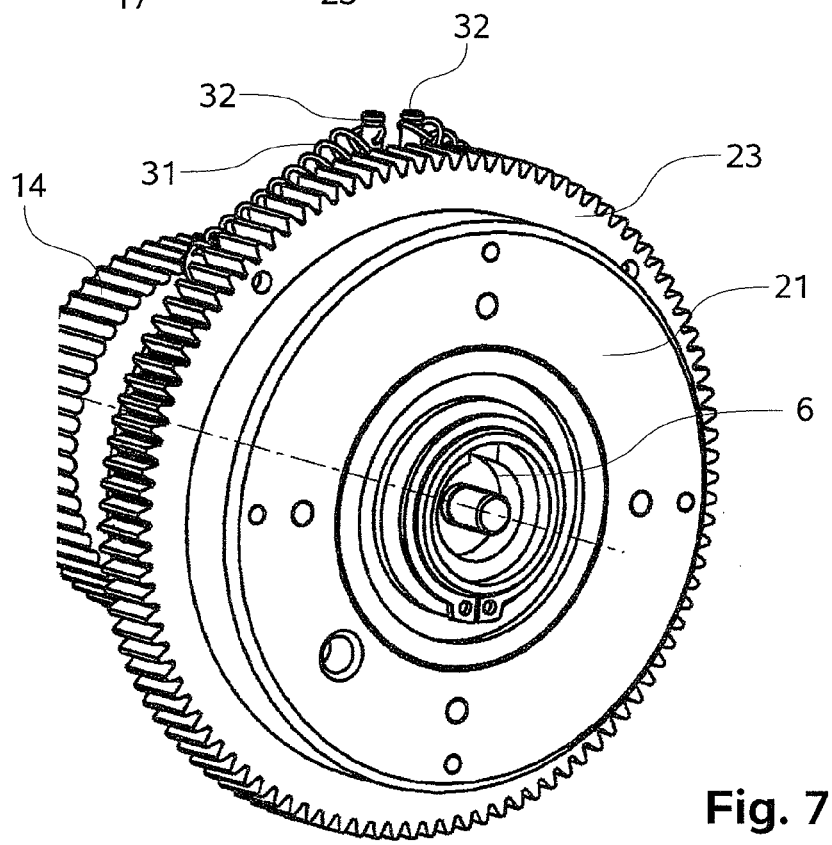

FIG. 7 schematically shows in a perspective view the assembly of FIG. 6 viewed from the other side.

Figure 8:
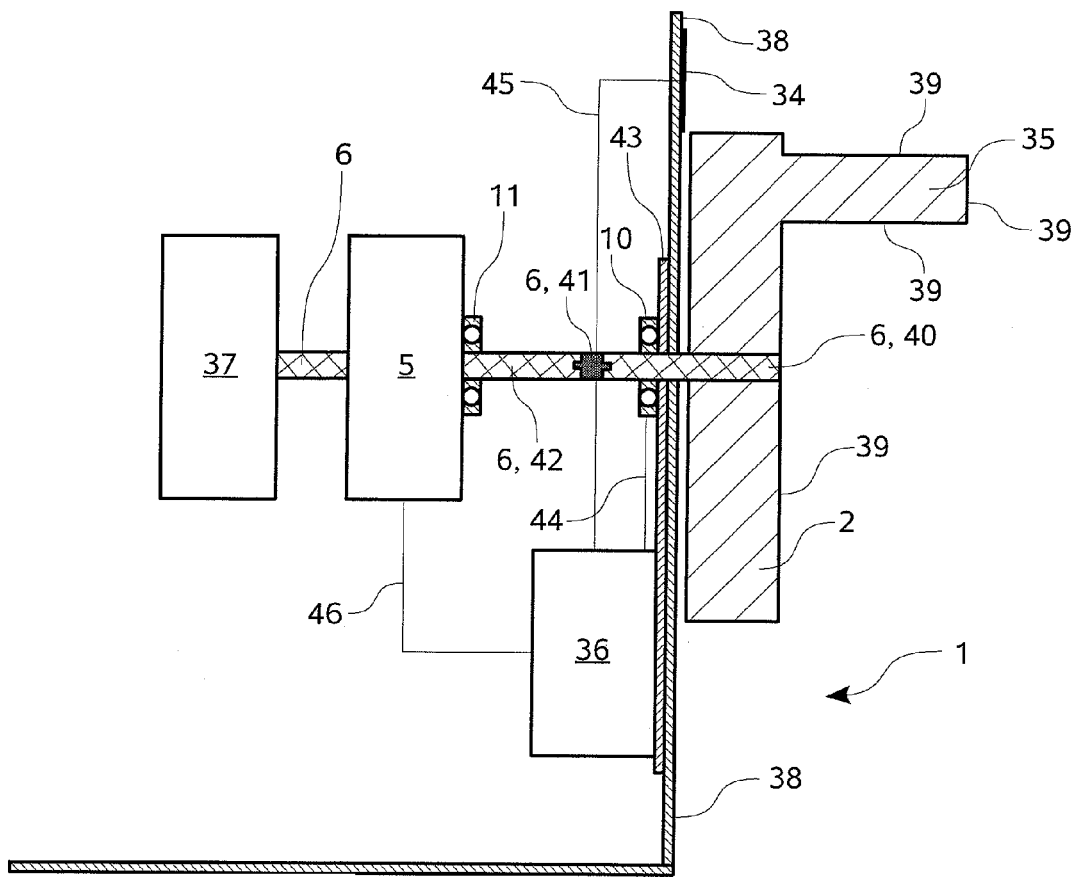

FIG. 8 schematically shows in a sectional view a part of a microtome with an embodiment of a sensor unit.

Equal or similar component parts are identified by identical reference signs in the Figures.

FIG. 1 shows a microtome 1 which is designed in the form of a rotary microtome. The microtome 1 has an actuating element 2, a movement mechanism not illustrated in FIG. 1 and a non-illustrated brake. The actuating element 2 is designed in the form of a handwheel and can be manually rotated by an operator. As a result thereof, with the movement mechanism provided inside the microtome, the holder 3 for the object head (not illustrated) is moved upwards and downwards in vertical direction. Due to this vertical movement of the holder 3, the (non-illustrated) object head mounted on the holder 3 performs with an object to be cut a relative motion to a knife blade. Neither the knife blade nor the knife holder is shown in FIG. 1. The knife holder can be adapted to the microtome 1 at the mounting place 4 provided therefor.

FIG. 2 shows in a perspective view a part of a microtome with an inventive device 5 for braking a shaft 6. Here, the actuating element 2 which is formed comparably to the actuating element 2 from FIG. 1 is illustrated in broken lines. The actuating element 2 is arranged immediately adjacent to and within the microtome housing (not illustrated in FIG. 2). The actuating element 2 is fixed to the device 5 for braking a shaft 6 of the microtome with screws 22. The device 5 for braking the shaft 6 of the microtome has several component parts which are shown in a sectional view in FIG. 3.

In FIG. 3, a first bearing unit 8 can be fixed to the component part 7 fixed to the housing by means of screws which are not illustrated in FIG. 3, the screws being screwed into bores 9 from the left side. The first bearing unit 8 has a first bearing 10 with which the shaft 6 is rotatably mounted with respect to the component part 7 fixed to the housing or, respectively, the first bearing unit 8. On the first bearing unit 8, a second bearing unit 11 can be fixed with screws 12. The second bearing unit 11 has a second bearing 13. Thus, the shaft 6 is rotatably mounted with respect to the component parts 7, 8 and 11 fixed to the housing by the two bearings 10, 13. The spur gear 14 engaging the toothed belt 15 (shown in FIG. 2) is connected in a rotatably fixed manner to the shaft 6. By means of the toothed belt 15, the movement mechanism of the microtome which is not shown in FIGS. 2 to 7 is driven. In principle, the shaft 6 could directly and rigidly be connected to a movement mechanism of the microtome. This would, for example, be functional in the rotary microtome shown in FIG. 1. The arrangement shown in FIGS. 2 and 3 is specifically used in a cryostat microtome, where the component parts shown in FIGS. 2 and 3 are arranged on the outer housing of the cryostat microtome and where a further spur wheel (not shown) is engaged with the toothed belt 15. By means of a further shaft (not shown) of this further spur wheel, eventually the movement mechanism of the cryostat microtome not shown in FIGS. 2 and 3 can be driven.

On the second bearing unit 11, a coil 16 of an electromagnet is arranged. In this embodiment, the actuator is designed in the form of an electromagnet. The sleeve-shaped component part 17 is likewise connected to the shaft 6 in a rotatably fixed manner. The sleeve-shaped component part 17 can be moved or displaced in the longitudinal direction of the shaft 6 by some millimeters. The rotatably fixed connection between the sleeve-shaped component part 17 and the shaft 6 is formed by external teeth on the area 18 of the shaft 6, which engage in complementarily formed internal teeth of the sleeve-shaped component part 17. The external teeth of the shaft 6 are extended by an additional displacement distance so that the sleeve-shaped component part 17 can be displaced with respect to the shaft 6 in the rotatably fixed state in axial direction. On the sleeve-shaped component part 17, two bearings 19, 20 are provided, with which the mounting ring 21 is rotatably mounted with respect to the sleeve-shaped component part 17. The sleeve-shaped component part 17 is arranged movably in the sense of a slide bearing connection with respect to the two bearings 19, 20 in axial direction, i.e. in the longitudinal direction of the shaft 6. On the mounting ring 21, the actuating element 2 is fixed with screws 22. Further, the toothed wheel 23 provided with external teeth is fixed to the mounting ring 21 by means of screws 24.

By the left part of the sleeve-shaped component part 17, the braking unit is realized, the braking unit being identified with the reference sign 25 in the following. Thus, the surface facing the second bearing unit 11 in axial direction has a toothing in the outer edge region, which toothing can be engaged with a toothing likewise provided in the outer edge region and arranged on the second bearing unit 11. Since the toothings are not explicitly illustrated in FIG. 3, it is indicated with the circle 26 shown in broken lines where the toothings of the second bearing unit 11 or, respectively, of the sleeve-shaped component part 17 are arranged. In any case, the sleeve-shaped component part 17 can be engaged with the second bearing unit 11 in a form-fitting manner.

The right part of the sleeve-shaped component part 17 has the first coupling area, which is designed in the form of a toothing. The toothing is formed on the outer edge region and on the surface of the sleeve-shaped component part 17 facing the mounting ring 21. The surface of the mounting ring 21 lying opposite to the toothing of the sleeve-shaped component part 17 also comprises a toothing which forms the second coupling area. The two toothings or the two coupling areas are substantially complementarily formed with respect to one another and can likewise be engaged with one another. Since these toothings are likewise not explicitly shown in FIG. 3, it is indicated by the circle 27 illustrated in broken lines where the toothings of the sleeve-shaped component part 17 and, respectively, of the mounting ring 21 are arranged. In any case, the sleeve-shaped component part 17 can be engaged with the mounting ring 21 in a form-fitting manner.

The sleeve-shaped component part 17 is biased such by means of a spring not shown in FIG. 3 that the two coupling areas are engaged with one another if the actuator or, respectively, the coil 16 of the electromagnet is deactivated. Then, the toothings of the braking unit 25 are not engaged with one another. In this operating state, the actuating element 2, the mounting ring 21, the sleeve-shaped component part 17 and the shaft 6 are connected to one another in a rotatably fixed manner. In this operating state, the brake is deactivated and the actuation or rotation of the actuating element 2 results in a rotation of the shaft 6, and thus via the spur wheel 14 the toothed belt 15 and eventually the movement mechanism of the microtome is driven.

If the electromagnet or the actuator is activated by supplying a current to the coil 16, the sleeve-shaped component part 17 is pulled to the left opposite to the biasing force of the spring so that the two coupling areas between the sleeve-shaped component part 17 and the mounting ring 21 are no longer engaged with one another and the toothing between the second bearing unit 11 and the sleeve-shaped component part 17 are engaged with one another. In this operating state, the actuating element 2, the mounting ring 21, the sleeve-shaped component part 17, the second bearing unit 11, the first bearing unit 8 and the component part 7 fixed to the housing are connected to one another in a rotatably fixed manner. As a result of the rotatably fixed connection between the sleeve-shaped component part 17 and the shaft 6, thus, the shaft 6, too, is locked or blocked with respect to the housing of the microtome. Accordingly, the spur wheel 14 and thus the toothed belt 15 cannot be moved, and the movement mechanism of the microtome is blocked. In other words, by means of the actuator the sleeve-shaped component part 17 is moved to the left in longitudinal direction of the shaft 6 in order to be locked with respect to the housing. If the actuator is not activated, the sleeve-shaped component part 17 is moved to the right due to the bias of the spring so that the sleeve-shaped component part 17 is connected in a rotatably fixed manner to the mounting ring 21 and thus to the actuating element 2.

The toothed wheel 23 is connected in a rotatably fixed manner to the actuating element 2. It can be taken from FIG. 2 that the toothed wheel 23 meshes with the toothed wheel 28. If the toothed wheel 28 is rotated as a result of the rotation of the actuating element 2 and of the toothed wheel 23, the rotation is detected with the incremental encoder 29 and is forwarded to a control unit not illustrated in FIGS. 2 to 7.

Thus, if the brake is deactivated and the actuating element 2 is rotated together with the shaft 6, the toothed wheel 23 rotates the toothed wheel 28, which can be detected by the incremental encoder 29.

If the brake is activated, that is the sleeve-shaped component part 17 is engaged with the second bearing unit 11 in a form-fitting manner, the actuating element 2, the mounting ring 21 and the toothed wheel 23 can be rotated with respect to the sleeve-shaped component part 17 —owing to the two bearings 19, 20 —since the two coupling areas are no longer engaged with one another. As a result thereof, however, also the toothed wheel 28 is rotated so that via the incremental encoder 29 corresponding signals can be transmitted to the control unit. These signals indicate to the control unit that the operator actuates or, respectively, rotates the actuating element 2 although the brake is activated. Since it can be assumed that at least one hand of the operator—intentionally—actuates the actuating element 2 and thus a risk of injury for the operator can be ruled out, the actuator is deactivated by the control unit. As a result thereof, due to the spring bias the sleeve-shaped component part 17 is forced to the right so that the actuating element 2 is connected via the mounting ring 21, the two coupling areas and the sleeve-shaped component part 17 to the shaft 6 in a rotatably fixed manner and that the movement mechanism of the microtome can thus be actuated again. Insofar, by the just described interaction between the sleeve-shaped component part 17, the toothed wheels 23, 28 and the incremental encoder 29 the actuating unit is formed, with which it can be determined whether the operator actuates the actuating element 2 with his/her hand when the brake is activated. Specifically, the actuating unit is formed in one piece with the brake unit with regard to the coupling area of the sleeve-shaped component part 17.

Since a predeterminable rotary position between the actuating element 2 and the movement mechanism of the microtome is provided, it is provided in that embodiment to rule out a possible rotation between the actuating element 2 and the sleeve-shaped component part 17 and thus with respect to the shaft 6, or at least to keep it small. It can be taken from FIGS. 4 to 7 that here two biasing means designed in the form of springs 30, 31 are provided, with which a rotation between the actuating unit and the actuating element 2 can be forced into a predeterminable angular position, namely a centered angular position. With one end, each of the springs 30, 31 acts on pins 32 on the actuating unit and, respectively, the sleeve-shaped component part 17 and, with the other end, they each act on pins 32 on the toothed wheel 23 which is connected in a rotatably fixed manner to the actuating element 2. Here, the two springs 30, 31 are arranged such that the one spring 30 causes a rotation between the sleeve-shaped component part 17 and the actuating element 2 in a substantially opposite rotary direction with respect to the other spring 31. The rotation between the sleeve-shaped component part 17 and the actuating element 2 can be limited by stops 33, which are only indicated in FIG. 6 in broken lines. The two stops 33 are each likewise formed in the form of a pin and are arranged in the toothed wheel 23 substantially parallel to the pins 32 fixed in the toothed wheel 23.

By means of the just described actuating unit, an actuation of the actuating element 2 is detected substantially mechanically. According to the embodiment of FIG. 8, an actuating unit is provided which is based on an electrical detection principle. For this, the sensor unit 34 is provided which is arranged adjacent to the actuating element 2. The sensor unit 34 is also shown in FIG. 1. By means of the sensor unit 34, a contact of the actuating element 2 by the operator can be determined when the operator, when grasping the handle 35, also contacts the sensor unit 34. When the sensor unit 34 detects or determines that it is contacted by the operator, the brake is controlled accordingly. That is, if the brake was activated, the brake is automatically released. If the sensor unit 34 does not detect any contact by the operator, the brake is automatically activated so that a relative motion between the object and the knife blade is not possible.

Merely shown in broken lines in FIG. 1, it is indicated that a control unit 36 is provided which is electronically connected to the sensor unit 34 and the brake. With the aid of a sensor unit 34, a first signal is generated if an operator contacts the sensor unit 34. The sensor unit 34 feeds the first signal to the control unit 36. Hereupon, the control unit 36 generates at least one signal for deactivation of the brake and feeds this signal to the brake.

If an operator does not contact the sensor unit 34, the sensor unit 34 does not generate a signal. The control unit 36 is programmed such that in such a case a corresponding signal is automatically generated for activation of the brake and is fed to the brake.

The sensor unit 34 has an electrically conductive area which is designed in the form of a hot embossing foil of stainless steel. The hot embossing foil of stainless steel is arranged electronically insulated with respect to further components of the microtome 1. The hot embossing foil of stainless steel is connected to an electrical circuit of the control unit 36. With the aid of the electrical circuit of the control unit 36, a contact of the electrically conductive area can be determined and the automatic brake can be controlled accordingly. The sensor unit 34 is designed in the form of a contact sensor.

FIG. 8 shows in a sectional view a part of a microtome 1 according to a further embodiment. The microtome 1 according to FIG. 8 is a rotary microtome which has an actuating element 2 designed in the form of a handwheel. The actuating element 2 is connected in a rotatably fixed manner to a shaft 6 driving the movement mechanism 37. The shaft is rotatably mounted relative to the microtome housing 38 with the aid of two bearings 10, 11.

Both the surface of the actuating element 2 and the surface of the handle 35 have a sensor unit 39. The sensor unit 39 has a foil contact sensor. The shaft 6 is formed in several pieces and has a first area 40, a second area 41 and a third area 42. The first area 40 and the third area 42 are formed electrically conductive. The second area 41 is formed electrically non-conductive. The first area 40 of the shaft 6 is in electrical contact with the sensor unit 39 and the bearing 10. The bearing 10 is electrically insulated relative to the microtome housing 38 by the insulating layer 43 from the rest of the components of the microtome 1. However, the bearing 10 is electrically connected to the control unit 36 via the connection line 44. Thus, the sensor unit 39, the first area 40 of the shaft 6 and the bearing 10 have the same electric potential which can be detected by the control unit 36. When an operator contacts the actuating element 2 or the handle 35, this can thus be detected by the control unit 36 and the brake can be controlled accordingly depending thereon. Between the first area 40 and the third area 42 of the shaft 6, the second, electrically non-conductive area 41 is arranged. With the second area 41 of the shaft 6, thus also the sensor unit 39, the actuating element 2, the handle 35, the first area 40 of the shaft 6 and the bearing 10 can be electrically insulated from the remaining components of the microtome 1.

The sensor unit 34 designed in the form of a hot embossing foil of stainless steel is electrically connected to the control unit 36 by means of the connection line 45. Thus, the microtome 1 from FIG. 8 has two sensor units 34 and 39. When an operator contacts one of the sensor units 34, 39 or both sensor units 34, 39, the brake which brakes the object head is automatically released.

The control unit 36 is connected via the connection line 46 to the device 5 for braking. The device 5 for braking from FIG. 8 is merely schematically illustrated and substantially has a component part fixed to the housing, an actuator designed in the form of an electromagnet and a spur wheel which is connected in a rotatably fixed manner to the third area 42 of the shaft 6. These components substantially correspond to the second bearing unit 11 fixed to the housing, the coil 16 and the sleeve-shaped component part 17 from FIG. 3. In other words, the device 5 for braking is merely composed of those components required for locking the shaft 6 with respect to the housing 38 of the microtome 1.

On the left-hand side of the device 5 for braking the shaft 6 and driven by the shaft 6, the movement mechanism 37 is schematically indicated, with which the relative motion between the object to be cut and the knife blade of the microtome 1 can be performed.

In FIG. 1, a locking lever 47 that can be mechanically actuated by an operator and is provided on the actuating element 2 or the handwheel is shown. With the locking lever 47, the handwheel and thus the movement mechanism and eventually also the object head can be mechanically locked in that a part of the locking lever 47 (not shown) engages a recess (not shown) on the microtome 1 in a form-fitting manner and thus locks the handwheel with respect to the microtome housing. Since this requires an additional hand movement or work step, the locking lever 47 can be dispensed with since the microtome 1 according to FIG. 1 has an inventive device for braking a shaft of a microtome.

According to the present embodiments, the device for braking or locking a shaft of a microtome can be switched between two states. In a first state, a rotatably fixed connection between the component parts 2 and 6 (see, for instance, FIG. 3) is given. In this state, the brake is deactivated. In a second state, a rotatably fixed connection between the component parts 6 and 8 (see, for instance, FIG. 3) is given and the component part 2 is separated from the component part 6. In this state, the brake is activated.

The actuating unit 17 serves to determine whether the operator actuates the actuating element 2 with his/her hand. In this case, the actuator is controllable such that the braking unit 25 can be moved out of the brake position. The actuating unit 17 has a first coupling area which can be engaged with a second coupling area, the second coupling area being connected in a rotatably fixed manner with the actuating element 2. The two coupling areas 27 are engaged with one another when the braking unit 25 is not engaged with the housing 11, the actuating unit 17 being connected in a rotatably fixed manner to the shaft. The actuating unit 17 is rotatably mounted with respect to the actuating element 2 if the two coupling areas 27 are not engaged with one another.

Accordingly, the device for braking or locking a shaft of a microtome is characterized by an actuator and a braking unit, wherein the braking unit is connected in a rotatably fixed manner to the shaft and wherein the braking unit can be automatically placed by the actuator in a brake position in which the shaft can be connected to the housing in a rotatably fixed manner and is rotatable with respect to the actuating element, wherein the movement mechanism 37 for performing the relative motion between the object and the knife blade can be driven via the shaft when the actuator has not placed the braking unit into the brake position.

LIST OF REFERENCE SIGNS

1 microtome
2 actuating element
3 holder for an object head
4 mounting place for a knife holder
5 device for braking of (6) of the microtome
6 shaft with which (5) can be braked
7 component part fixed to the housing
8 first bearing unit
9 bore
10 first bearing
11 second bearing unit
12 screw
13 second bearing
14 spur wheel, connected to (6) in a rotatably fixed manner
15 toothed belt
16 coil
17 sleeve-shaped component part
18 area of (6) or (17) with toothing
19 bearing
20 bearing
21 mounting ring
22 screw
23 toothed wheel
24 screw
25 braking unit
26 edge region of (11) and (17), at which the toothings are arranged
27 edge region at which the coupling areas of (17) and (21) are arranged
28 toothed wheel
29 incremental encoder
30 spring or biasing means
31 spring or biasing means
32 pins for (30) or, respectively, (31)
33 stop
34 sensor unit
35 handle of (2)
36 control unit
37 movement mechanism
38 microtome housing
39 sensor unit
40 first area of (6)
41 second area of (6)
42 third area of (6)
43 insulating layer
44 connection line between (10) and (36)
45 connection line between (34) and (36)
46 connection line between (36) and (5)
47 locking lever

The invention claimed is:

1. A brake controlling device and microtome (1) having the shaft (6), an actuating element (2), a movement mechanism (37) and a housing (38), wherein with the movement mechanism (37) an object to be cut can be moved relative to a knife blade, wherein the actuating element (2) can be manually actuated by an operator and, as a result thereof, the shaft (6) can be rotated, and wherein via the shaft (6) the movement mechanism (37) for performing the relative motion between the object and the knife blade can be driven, an actuator and a braking unit, wherein the braking unit is connected to the shaft (6) in a rotatably fixed manner and wherein with the actuator the braking unit can be automatically placed in a brake position in which the shaft (6) can be connected to the housing (38, 7) in a rotatably fixed manner, an actuating unit (17) configured to determine whether the operator manually actuates the actuating element (2) and, disengage the braking unit (25) from the brake position, wherein the actuating unit (17) has a first coupling area which can be engaged with a second coupling area, in that the second coupling area is connected in a rotatably fixed manner to the actuating element (2), and in that the two coupling areas (27) are engaged with one another when the braking unit (25) is not engaged with the housing (11), wherein in that the actuating unit (17) is connected to the shaft in a rotatably fixed manner, in that the actuating unit (17) is mounted rotatably with respect to the actuating element (2) when the two coupling areas (27) are not engaged with one another when the braking unit (25) is engaged with the housing (11).

2. The device according to claim 1, characterized in that the braking unit is frictionally or positively engaged with the housing (38) or a component part (7, 8, 11) fixed to the housing in the brake position.

3. The device according to claim 1, characterized in that the braking unit (25) has a component part, in particular a sleeve (17) or a spur wheel, which has a toothing in radial or in axial direction, in that the toothing engages with a substantially complementarily formed toothing provided on the housing or on the component part (11) fixed to the housing if the braking unit (25) is in the brake position.

4. The device according to claim 1, characterized in that the actuator has an electromagnet with which the braking unit can be moved, in particular attracted.

5. The device according claim 1, characterized in that the braking unit (25) is biased or biased with a spring such that the braking unit (25) is forced into the brake position and in that the actuator counteracts the biasing force when moving the braking unit (25) out of the brake position.

6. The device according to claim 1, characterized in that the braking unit (25) is biased or biased with a spring such that the braking unit (25) is forced out of the brake position and in that the actuator counteracts the biasing force when placing the braking unit (25) into the brake position.

7. The device according to claim 1, characterized in that at least one biasing means (30, 31) is provided, with which a rotation between the actuating unit (17) and the actuating element (2) can be forced into a predeterminable angular position or a centered angular position.

8. The device according to claim 7, characterized in that the at least one biasing means has a spring (30, 31) which on the one end acts on the actuating unit (17) and which on the other end acts on the actuating element (2).

9. The device according to claim 8, characterized in that two springs (30, 31) are provided and arranged such that the one spring (30) causes a rotation between the actuating unit (17) and the actuating element (2) in a substantially opposite rotary direction to the other spring (31).

10. The device according to claim 1, characterized in that the actuating unit (17) is connected in a rotatably fixed manner to the braking unit (25) or in that the actuating unit (17) is formed in one piece with the braking unit.

11. The device according to claim 1, characterized in that a movement sensor (29) is provided with which a movement of the actuating element (2) or the actuating unit (17) can be detected.

12. The device according to claim 11, characterized in that the movement sensor has an incremental encoder provided on the actuating element (2) or in that on the actuating element (2) a toothing (23) is provided which meshes with a toothed wheel (28) on which an incremental encoder (29) is provided.

13. The device according to claim 1, characterized in that a control unit (36) is provided which is connected, or electronically connected to the actuator and the movement sensor (29).

14. The device according to claim 1, characterized in that the actuating unit has at least one sensor unit (34, 39) which is provided on the actuating element (2) or adjacent to the actuating element (2), with which a contact by the operator can be determined, and in that the brake is controllable depending on a contact by the operator determined or not determined by the at least one sensor unit (34, 39).

15. The device according to claim 14, characterized in that the sensor unit (34, 39) has an electrically conductive area or a hot embossing foil of stainless steel—which is arranged electronically insulated with respect to further components of the microtome (1) and which is connected to an electrical circuit (36), and in that with the electrical circuit (36) a contact of the electrically conductive area can be determined.

16. The device according to claim 14, characterized in that the sensor unit (34, 39) has a proximity sensor, a contact sensor, a foil contact sensor or a capacitive sensor.

17. The device according to claim 14, characterized in that the actuating element (2) has a handwheel, in that the actuating element (2) is connected in a rotatably fixed manner to a shaft (6) driving the movement mechanism (37), and in that the shaft (6) is rotatably mounted relative to the microtome housing (38) by at least one bearing (10, 11).

18. The device according to claim 1, characterized in that the microtome (1) is designed in the form of a rotary microtome, a slide microtome, a vibratome or a disc microtome.

19. The device according to claim 1, characterized in that the rotation between the actuating element (2) and the actuating unit (17) is limited by stops (33).

20. A method for controlling a device for braking a shaft of a microtome, in particular for operating a device according to one of the claim 1, wherein the microtome (1) has the shaft (6), an actuating element (2), a movement mechanism (37) and a housing (38), wherein with the movement mechanism (37) an object to be cut is moved relative to a knife blade, wherein the actuating element (2) is manually actuated by an operator and, as a result thereof, the shaft (6) is rotated, and wherein via the shaft (6) the movement mechanism (37) for performing the relative motion between the object and the knife blade is driven, providing the device with an actuator and a braking unit (25), wherein the braking unit (25) is connected in a rotatably fixed manner to the shaft (6), wherein with the actuator the braking unit (25) is automatically placed in a brake position in which the shaft (6) is connected in a rotatably fixed manner to the housing (38), determining whether the operator manually actuates the actuating element (2) with an actuating unit (17), the actuating unit (17) having a first coupling area which can be engaged with a second coupling area, in that the second coupling area is connected in a rotatably fixed manner to the actuating element (2), disengaging the braking unit (25) from the brake position when the actuation of the actuating element by the operator is determined, the brake unit (25) being disengaged by engaging the two coupling areas (27) with one another, engaging the braking unit (25) into the brake position when the actuation of the actuating element by the operator is not determined, the brake unit (25) being engaged by disengaging the two coupling areas (27) with one another.

* * * * *

UNITED STATES PATENT AND TRADEMARK OFFICE
CERTIFICATE OF CORRECTION

PATENT NO. : 8,353,232 B2  
APPLICATION NO. : 12/602183  
DATED : January 15, 2013  
INVENTOR(S) : Walter et al.

Page 1 of 1

It is certified that error appears in the above-identified patent and that said Letters Patent is hereby corrected as shown below:

On the Title Page, item (30) insert:

--(30) Foreign Application Priority Data  
Jun. 6, 2007   (DE) …………………… 10 2007 026 844.2--

Signed and Sealed this  
Seventeenth Day of September, 2013

Teresa Stanek Rea  
*Deputy Director of the United States Patent and Trademark Office*